(12) United States Patent
Reetz et al.

(10) Patent No.: US 6,316,675 B1
(45) Date of Patent: Nov. 13, 2001

(54) PROCESS FOR THE PREPARATION OF AN OLEFIN-SUBSTITUTED AROMATIC OR HETEROAROMATIC COMPOUND

(75) Inventors: Manfred T. Reetz; Gunther Lohmer; Renate Lohmer, all of Mülheim an der Ruhr (DE)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 0 days.

(21) Appl. No.: 09/402,003

(22) PCT Filed: Mar. 17, 1998

(86) PCT No.: PCT/EP98/01532

§ 371 Date: Sep. 23, 1999

§ 102(e) Date: Sep. 23, 1999

(87) PCT Pub. No.: WO98/42644

PCT Pub. Date: Oct. 1, 1998

(30) Foreign Application Priority Data

Mar. 25, 1997 (DE) .............................. 197 12 388

(51) Int. Cl.[7] .............................. C07C 2/86; C07C 41/30; C07C 67/343

(52) U.S. Cl. .............. 568/335; 568/630; 568/632; 568/939; 585/419; 585/425; 585/426; 585/428; 585/429; 585/442; 585/457; 585/466; 585/467; 585/577; 585/660; 585/661

(58) Field of Search .................... 585/419, 425, 585/426, 428, 429, 442, 457, 466, 467, 527, 660, 661; 568/335, 632, 630, 939

(56) References Cited

U.S. PATENT DOCUMENTS 4,879,426  11/1989  Larock et al. ........................ 585/467

FOREIGN PATENT DOCUMENTS 195 06 442  8/1996  (DE) .
0 103 544   3/1984  (EP) .
0 709 357   5/1996  (EP) .

Primary Examiner—Floyd D. Higel
(74) Attorney, Agent, or Firm—Norris McLaughlin & Marcus

(57) ABSTRACT

A process for the synthesis of olefins having aromatic substituents is described in which olefins are reacted with aryl halides in the presence of catalysts consisting of palladium compounds and tetraaryl phosphonium salts.

15 Claims, 2 Drawing Sheets

Figure 1:
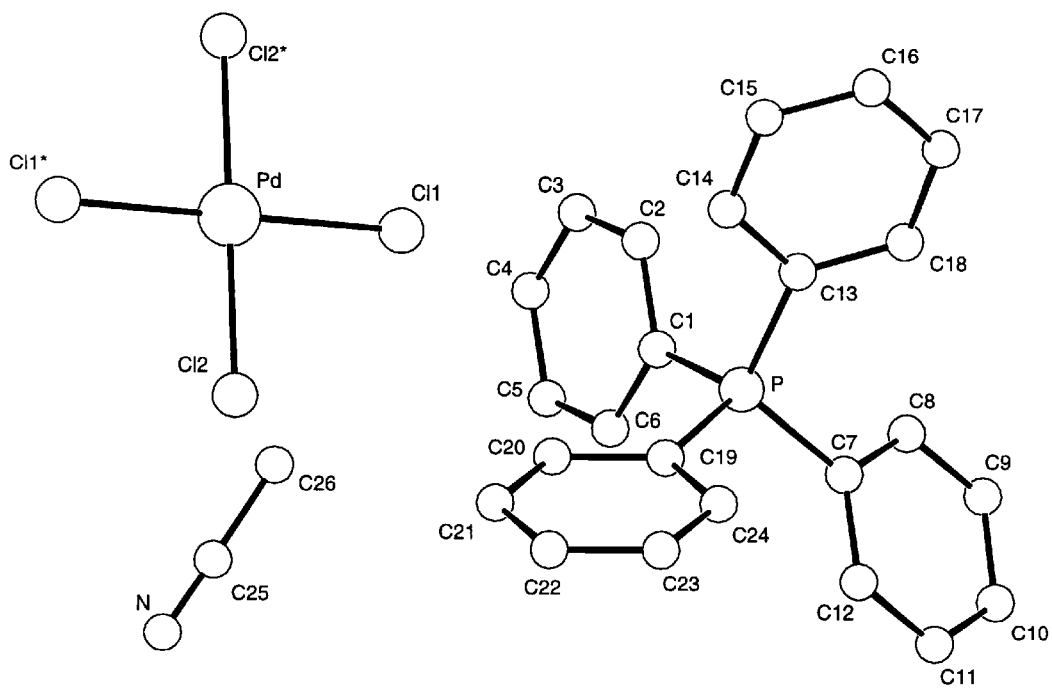

X-ray crystal structure of (PPh$_4$)$_2$PdCl$_4$ from Example A with one molecule of acetonitrile in the crystal.

X-ray crystal structure of trans-bis(N,N-dimethylglycinato)palladium from Example D with one molecule of water in the crystal.

PROCESS FOR THE PREPARATION OF AN OLEFIN-SUBSTITUTED AROMATIC OR HETEROAROMATIC COMPOUND

This application is a 371 of PCT/EP98/01532, which was filed on Mar. 17, 1998.

The present invention relates to a novel process for the synthesis of oletins having aromatic substituents using a novel and particularly active palladium-containing catalyst system, optionally in the presence of selectivity-enhancing additives.

In industrial chemistry, oletins having aromatic substituents play an important role, e.g., as starting materials for polymers, sunscreen agents (UV absorbers), fine chemicals and prodrugs.

A known method for the preparation of such olefins is the so-called Heck reaction in which iodo- or bromoaromatics ArX (X=I, Br) and, in rare cases, chloroaromatics (X=Cl) are reacted with oletins in the presence of stoichiometric amounts of a base and catalytic amounts of a palladium compound (F. Heck, "Vinyl Substitutions with organopalladium Intermediates" in Comprehensive Organic Syntheses, Vol. 4, Pergamon Press, Oxford, 1991, p. 833; R. F. Heck, Palladium Reagents in Organic Syntheses, Academic Press, London, 1985; R. F. Heck, Org. React. (N.Y.) 1982, 27, 345; A. de Meijere, F. E. Meier, Angew. Chem. 1994, 106, 2473; J. Tsuji, Palladium Reagents and Catalysts: Innovations in Organic Synthesis, Wiley, Chichester, 1995).

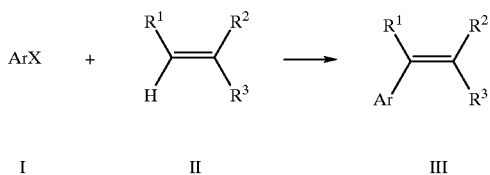

However, the Heck reaction has not been used for industrial application to date (B. Cornils, W. A. Herrmann, Applied Homogeneous Catalysis with Organometallic Compounds, VCH, Weinheim, 1996). This is due to the fact, inter alia, that the reactivity of haloaromatics ArX decreases very fast in the order ArI>ArBr>ArCl. Thus, in the research field, the reactive iodoaromatics are employed usually; for industrial application, however, they are much too expensive or difficult to obtain. The common catalysts and precatalysts, such as palladiumtetrakis(triphenylphosphane) $Pd(PPh_3)_4$ or $Pd(OAc)_2$ in the presence of excess $PPh_3$, give significantly lower yields in the case of bromoaromatics while the reactions of the chloroaromatics, which are available in particularly large amounts in the industry, proceed with completely unsatisfactory yields. As a cause thereof, Heck states the formation of tetraarylphosphonium compounds whereby the catalyst is decomposed with the precipitation of elemental Pd powder (R. F. Heck, Org. React. (N.Y.) 1982, 27, 345; C. B. Ziegler, R. F. Heck, J. Org. Chem. 1978, 43, 2941). Indeed, catalytic C—C bond formation processes with inert chloroaromatics, especially in terms of Heck reactions, are considered a special challenge (V. V. Crushin, H. Alper, Chem. Rev. 1994, 94, 1047; B. Cornils, W. A. Herrmann, Applied Homogeneous Catalysis with Organometallic Compounds, VCH, Weinheim, 1996).

The Heck reaction of chlorobenzene with styrene to form trans-stilbene proceeds to 60% when 1 mole % $Pd(OAc)_2$ is used in the presence of 2 mole % of the ligand 1,4-bis(diisopropylphosphino)butane (Y. Ben-David, M. Portnoy, M. Gozin, D. Milstein, Organometallics 1992, 11, 1995) This is among the best results reported in the literature, but it has not been transferred to electron-deficient olefins, such as acrylates, since the highly nucleophilic phosphane initiates undesired polymerizations. Another particular disadvantage is the fact that relatively large amounts of an expensive (or difficult-to-obtain) ligand which is sensitive to oxidation are required. Further, transfer to other substrates was successful only in single cases. Thus, for example, the reaction of styrene with 4-chlorotoluene proceeds to only 50% (Y. Ben-David, M. Portnoy, M. Gozin, D. Milstein, Organometallics 1992, 11, 1995).

The use of Pd salts, such as $Pd(OAc)_2$, in the presence of excess tris(o-tolyl)phosphane $P(o-Tol)_3$ involves an active catalyst system with which the Heck reaction of bromoaromatics, especially if activated by electron-withdrawing substituents, proceeds with little satisfactory to good yields (20–90%) (A. Spencer, J. Organomet. Chem. 1983, 258, 101; J. Organomet. Chem. 1984, 270, 115; EP 0078768 A1 and EP 0103544 A1). In contrast, activated chloroaromatics react with quite poor yields. At any rate, the tact that $P(o-Tol)_3$ is an expensive and difficult-to-obtain phosphane is a drawback.

In more recent works, it is reported that certain palladacycles prepared from $Pd(OAc)_2$ and $P(o-Tol)_3$ are unusually active catalysts in the Heck reaction. Thus, even non-activated bromoaromatics, such as bromobenzene or bromoanisole, could be reacted with n-butyl acrylate to form the corresponding Heck products (94–96%) (W. A. Herrmann, C. Broßmer, W. Öfele, C.-P. Reisinger, T. Priermeier, M. Beller, H. Fischer, Angew. Chem. 1995, 107, 1989; DE 4421730 C1 and EP 0725049 A1). However, transfer to chloroaromatics was only partially successful. Only activated chloroaromatics, such as 4-chlorobenzaldehyde, could be reacted with n-butyl acrylate (81%), and only in the presence of a tenfold excess of tetrabutylammonium bromide as an additive. Non-activated chloroaromatics, such as chlorobenzene, 4-chloroanisole or chlorotoluene, could not be made to react. Another disadvantage of all these reactions is the fact that the expensive and difficult-to-obtain tris(o-tolyl)phosphane must be employed in the preparation of the catalyst.

Also, there have been numerous attempts to employ Pd-containing heterogeneous catalysts in the Heck reaction. While the results are altogether acceptable for the use of iodoaromatics, no generally satisfactory solution to the problem exists to date in the case of bromo- or chloroaromatics (V. V. Grushin, A. Alper, Chem. Rev. 1994, 94, 1047). Thus, for example, moderate yields are obtained in the reaction of chlorobenzene with styrene using various supported Pd catalysts, even if a tenfold excess of chlorobenzene is used (M. Julia, M. Duteil, C. Grand, E. Kuntz, Bull. Soc. Chim. Fr. 1973, 2791; K. Kaneda, M. Higuchi, T. Imanaka, J. Mol. Catal. 1990, 63, L33). Undesired side-products include benzene and diphenyl.

Thus, it is clear that there is still an urgent need for simple or readily available palladium catalysts for the Heck reaction of chloro- and bromoaromatics.

The present invention provides a solution to the problems described above since it has surprisingly been found that compounds of the type of the above formula III are readily available using a Heck reaction. As catalysts, there are used common palladium(II) salts $PdXY$ or their $CH_3CN$, PhCN or $PPh_3$ complexes, wherein typically X=Y=Cl, Br, I, $RCO_2$ [R=$C_1$–$C_{22}$, $CF_3$, $CCl_3$, $CH_2N(CH_3)_2$, $C_6H_5$] or $RSO_3$ (R=$C_1$–$C_{22}$, $CF_3$, $C_4F_9$, $CCl_3$, $C_6H_5$, p—$CH_3C_6H_4$), or typically X=Cl, Br, I, $RCO_2$ (R=$C_1$–$C_{22}$, $CF_3$, $CCl_3$, $CH_2OCH_3$, $C_6H_5$), and typically Y=$C_6H_5$, o—, m—, p—$CH_3C_6H_4$, o-, m-, p—Cl—$C_6H_4$, o-, m-, p—$CHOC_6H_4$, o-, m-, p—CN—$C_6H_4$, o-, m-, p—$NO_2$—$C_6H_4$, o-, m-, p—PhCO—$C_6H_4$, o-, m-, p—F—$C_6H_4$, 1-$C_{10}H_7$ or 2-$C_{10}H_7$, which are mixed with tetraarylphosphonium salts $Ar^1Ar^2Ar^3Ar^4P^+Z^-$, wherein $Ar^1$, $Ar^2$, $Ar^3$ and $Ar^4$ represent identical or different aryl residues, typically Ar=$C_6H_5$, o-, m-, p—$CH_3$—$C_6H_4$, o-, m-, p—Cl—$C_6H_4$, o-, m-, p—CHO—$C_6H_4$, o-, m-, p—CN—$C_6H_4$, o-, m-, p—$NO_2$—$C_6H_4$, o-, m-, p—PhCO—$C_6H_4$, o-, m-, p—F—$C_6H_4$, 1-$C_{10}H_7$ or 2-$C_{10}H_7$, and Z=Cl, Br, $RCO_2$ (R=$C_1$–$C_{22}$, $CF_3$, $CCl_3$, $C_6H_5$) or $RSO_3$ (R=$C_1$–$C_{22}$, $CF_3$, $C_4F_9$, $C_6H_5$, p—$CH_3C_6H_4$). Preferably, $PdCl_2$, $PdCl_2(CH_3CN)_2$, $Pd(OAc)_2$, $C_6H_5PdCl$ or $C_6H_5PdCl.PPh_3$ or their dimeric or oligomeric forms are used in the presence of tetraphenylphosphonium chloride or bromide. The ratio of PdXY to $Ar^1Ar^2Ar^3Ar^4P^+Z^-$ ranges between 1:1 and 1:10, a ratio of 1:6 being preferably selected.

Aprotic dipolar solvents, such as dimethylformamide (DMF) dimethylacetamide (DMA), dimethylsulfoxide, propylene carbonate, 1,3-dimethyl-3,4,5,6-tetrahydro-2(1H)-pyrimidinone (DMPU) or 1-methyl-2-pyrrolidinone (NMP), preferably DMF or NMP, are used as the solvents.

Metal salts, such as sodium, potassium, cesium, calcium or magnesium salts of carboxylic acids, or the corresponding carbonates or bicarbonates, or amines, such as triethylamine or trioctylamine, preferably sodium acetate, are used as the base. The ratio of base to aryl halide ranges between 1:1 and 5:1, preferably 1.5:1 to 2:1.

As selectivity-enhancing additives, there are used nitrogen-containing carboxylic acids, such as common α- or β-amino acids $H_2N(R)CHCO_2H$ or $H_2N(R)CHCH_2CO_2H$ [R=H, $CH_3$, $C_6H_5$, $CH_2C_6H_4$, $CH(CH_3)_2$], or their N-alkylated forms $R'NH(R)CHCO_2H$ or $R'NH(R)CHCH_2CO_2H$, or $R'_2N(R)CHCO_2H$ or $R'_2N(R)CHCH_2CO_2H$ [R'=$CH_3$, $C_2H_5$, $C_3H_7$, $C_4H_9$, or R'+R'= $(CH_2)_4$ or $(CH_2)_5$], or their sodium or potassium salts, anthranilic acid or N,N-dimethylanthranilic acid, or pyridinecarboxylic acids (or their sodium or potassium salts), such as 2-pyridinecarboxylic acid, or aromatic nitrogen-containing heterocycles, such as pyridine, lutidine, 2,2'-dipyridyl or quinoline. Preferably, N,N-dimethylglycine is used. The ratio of additive to palladium ranges between 100:1 and 1:1, preferably between 50:1 and 1:1. The use of these additives results in a substantial or complete suppression of side-reactions with the undesired formation of reduction or coupling products, such as benzene or diphenyl (both from PhX), usually occurring in the Heck reaction, or undesired double Heck reactions with the olefin. Further, the selectivity for the trans-isomer is increased. The nitrogen-containing compounds may also be directly employed as an additive and at the same time as a base.

Reaction temperatures of between 60° C. and 180° C. may be selected; preferably, the reactions are allowed to proceed between 100° C. and 150° C.

As to the aryl component ArX, a wide variety of aryl and heteroaryl chlorides, bromides, o-tosylates, o-mesylates or o-triflates may be employed, for example, benzene, naphthalene, pyridine or quinoline derivatives.

In the olefin component of the above formula II, $R^1$, $R^2$ and $R^3$ are independently hydrogen, alkyl-($C_1$–$C_8$), phenyl, 1- or 2-naphthyl, vinyl, O-alkyl-($C_1$–$C_8$), O-phenyl, CN, $CO_2H$, $CO_2$-alkyl-($C_1$–$C_8$), $CO_2$-phenyl, $CONH_2$, CONH-alkyl-($C_1$–$C_5$), CON(alkyl)$_2$-($C_1$–$C_5$), fluoro, chloro, PO(phenyl)$_2$, PO(alkyl)$_2$-($C_1$–$C_5$), CO-phenyl, CO-alkyl-($C_1$–$C_5$), NH-alkyl-($C_1$–$C_4$), $SO_3H$, $PO_2H$, $SO_3$-alkyl-($C_1$–$C_4$) or $SO_2$-alkyl-($C_1$–$C_4$); further, cyclic derivatives are also possible, namely if $R^1$+$R^2$=$(CH_2)_n$ or $R^2$+$R^3$=$(CH_2)_n$, wherein n may be from 2 to 16.

EXAMPLES

The palladium catalysts used may be synthesized separately prior to the actual reaction, or generated in situ.

Example A

Preparation of $(Ph_4P)_2PdCl_4$ 70 mg (0.4 mmol) of $PdCl_2$ and 295.9 mg (0.79 mmol) of $Ph_4PCl$ in 4 ml of acetonitrile are heated at 115° C. with stirring for some minutes. Upon slowly cooling, 350.4 mg (0.38 mmol) of red-brown needles crystallize from the clear red-brown solution. Yield: 95.7%;

Empirical formula: $C_{48}H_{40}P_2Cl_4Pd$, M=927.02 g/mol; Elemental analysis: found [%]: 61.64 C, 4.60 H, 6.57 P, 15.83 Cl, 10.84 Pd calculated [%]: 62.19 C, 4.35 1H, 6.68 P, 15.30 Cl, 11.48 Pd; $^{31}$P NMR: δ=23.4 ppm (d$_7$-DMF).

X-ray Crystal Structure Analysis: FIG. 1

Example B

Preparation of $[PPh_3PdPh(\mu\text{-Cl})]_2$ 112.3 mg (0.50 mmol) of $Pd(OAc)_2$ and 375.3 mg (1.0 mmol) of $Ph_4PCl$ are dissolved in 10 ml of acetonitrile to give a red-brown solution which is stirred at room temperature for 30 minutes. After the addition of 0.5 ml of ethanol, the mixture is stirred in a closed vessel at 40° C. for 30 minutes. A light-green fine precipitate forms immediately and grows upon heating. The precipitate is isolated and dried under vacuum.

Yield: 95.2 mg (0.099 mmol, 39.6%); Empirical formula: $C_{48}H_{40}P_2Cl_2Pd_2$, M=962.54 g/mol; Elemental analysis:

found [%]: 59.60 C, 4.14 H, 6.77 P, 7.65 Cl, 22.05 Pd calculated [%]: 59.89 C, 4.19 H, 6.44 P, 7.37 Cl, 22.11 Pd;

Example C $[PPh_3PdPh(\mu\text{-Cl})]_2$+Na dimethylglycinate 48.3 mg (0.05 mmol) of $[PPh_3PdPh(\mu\text{-Cl})]_2$ and 13.0 mg (0.10 mmol) of Na dimethylglycinate are suspended in 2 ml of DMF. Upon heating to 70° C., a clear green solution forms.

$^{31}$P NMR: δ=31.2 ppm (d$_7$-DMF).

Example D

Preparation of trans-bis (N,N-dimethylglycinato) Pd 2.0 g (19.4 mmol) of dimethylglycine and 0.58 g (1.97 mmol) of sodium tetrachloropalladate are dissolved in 10 ml of water at room temperature. To the solution, which is orange in color, is added 0.473 g (8.43 mmol) of KOH. After 3 hours of stirring, the light yellow solution is concentrated to half its volume at room temperature, upon which yellow crystals precipitate. The crystals are recrystallized from hot methanol.

Yield: 0.403 g (1.2 mmol, 60.9%) Empirical formula: $C_8H_{14}N_4O_4Pd$, M=336.64 g/mol; Elemental analysis:

found [%]: 29.10 C, 4.22 H, 16.80 N, 31.3 Pd calculated [%]: 28.54 C, 4.19 H, 16.64 N, 19.01 0, 31.61 Pd.

Figure 2:
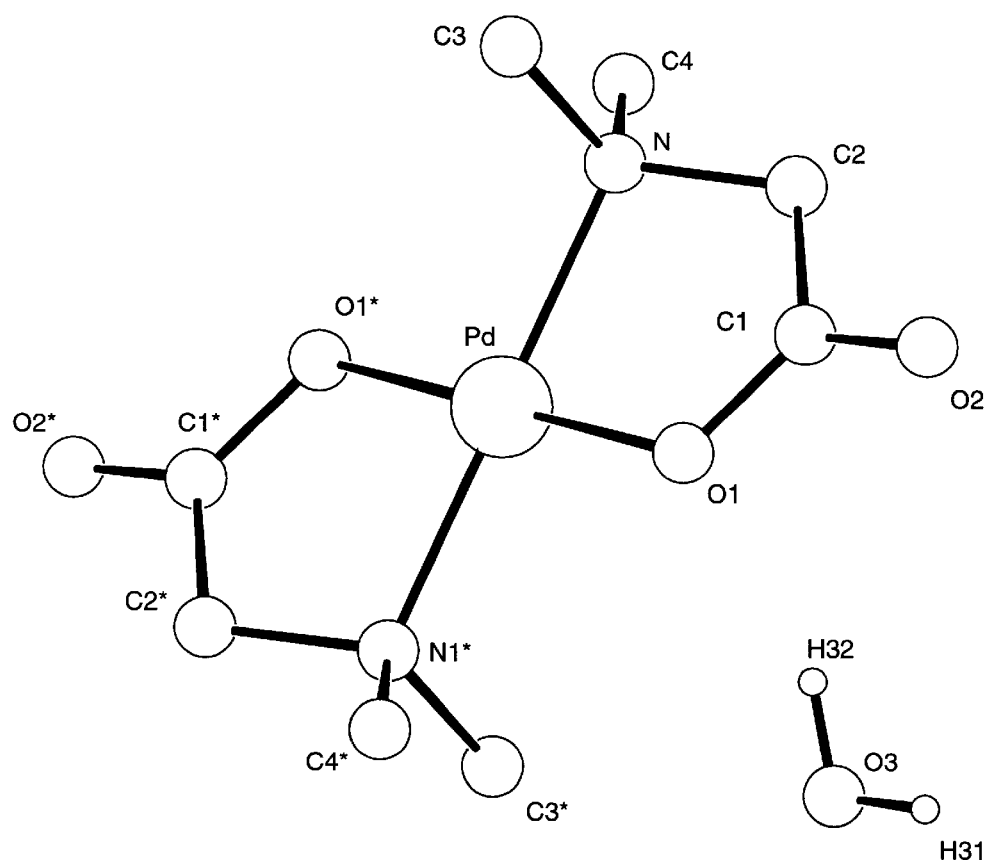

X-ray Crystal Structure Analysis: FIG. 2

Example E $(CH_3CN)_2PdCl_2$+6 $Ph_4PCl$+6 dimethylglycine 25.94 mg (0.1 mmol) of $(CH_3CN)_2PdCl_2$ and 224.89 mg (0.6 mmol) of $Ph_4PCl$ are dissolved in 5 ml of DMF together with 61.87 mg (0.6 mmol) of dimethylglycine. The clear orange solution is stirred at room temperature for 1 hour, the solvent is evaporated and recondensed under vacuum, and the residue is dried under high vacuum to leave 304.2 mg of an orange-brown solid having a Pd content of 3.32%.

Example F

Preparation of the Base $Ph_4POAc$

In a 100 ml round-bottom flask, 0.838 g (2.24 mmol) of phosphonium chloride and 0.365 g (2.19 mmol) of silver acetate are dissolved in 20 ml of water. After 1 hour, the voluminous AgCl precipitate is filtered off, and the water is removed in a rotary evaporator. The crystalline residue is taken up in ethanol and filtered over cotton wool. Half of the ethanol is removed to form a white crystalline solid.

Yield: 637.5 mg (1.6 mmol, 73.1%) $^1$H NMR (200 MHz, $d_7$-DMF): δ=1.5 (s), 3H, $CH_3$—; 7.4–7.9 (m), 20H, phenyl.
$^{13}$C NMR (50 MHz, $d_7$-DMP): δ=24.5 (s), $CH_3$—; 118.5, 130.9, 135.2, 135.8 (d) phenyl; 173.0 (s) COO—.

Examples with Styrene and Br- or Cl-aromatics

In the following Examples, the reactions were performed in a Schlenk vessel with a Young-Hahn seal, unless otherwise stated.

Example 1

To a reaction vessel standing on a scale, 5.2 mg (0.02 mmol) of $(CH_3CN)_2PdCl_2$ and 45.1 mg (0.12 mmol) of $Ph_4PCl$ are added, followed by two cycles of evacuation and flushing with argon. Under argon, 164 mg (2 mmol) of anhydrous sodium acetate, 114.8 mg (1.00 mmol) of chlorobenzene and 150.8 mg (1.45 mmol) of styrene are added. After the addition of 1 ml of NMP, the vessel is sealed, and the mixture is stirred first at 120° C. for 45 minutes and then at 150° C. for 11 hours.

After the reaction, the GC standards n-decane and n-hexadecane are added, and 3 ml of diethyl ether is added to the mixture. After filtering off the solids, the filtrate is examined by gas chromatography: With 78.5% conversion of Cl-benzene, an 80% yield of Heck products (86.5% trans-stilbene, 0.3% cis-stilbene, and 13.2% 1,1-diphenylethene) is obtained.

Example 2

A reaction is performed as described in Example 1, except that DMF is used as the solvent rather than NMP. Stirring is performed at 150° C. for 5.5 hours. With 78.99% conversion of Cl-benzene, a 72.1% yield of Heck products (86.1% trans-stilbene, 0.9% cis-stilbene, and 13.0% 1,1-diphenylethene) is obtained.

Example 3

A reaction is performed as described in Example 1, except that DMA is used as the solvent rather than NMP. Stirring is performed at 150° C. for 8 hours. With 55.2% conversion of Cl-benzene, a 61.2% yield of Heck products (83.8% trans-stilbene, 1.1% cis-stilbene, and 15.1% 1,1-diphenylethene) is obtained.

Example 4

A reaction is performed as described in Example 1, except that 10.3 mg (0.04 mmol) of $(CH_3CN)_2PdCl_2$, 59.7 mg (0.16 mmol) of $Ph_4PCl$, 157.6 mg (1.92 mmol) of anhydrous sodium acetate, 107.1 mg (0.95 mmol) of chlorobenzene and 136.2 mg (1.31 mmol) of styrene in 1 ml of DMF are reacted. Stirring is performed at 150° C. for 8 hours. With 95.6% conversion of Cl-benzene, a 70.4% yield of Heck products (84.9% trans-stilbene, 0.7% cis-stilbene, and 14.4% 1,1-diphenylethene) is obtained.

Example 5

A reaction is performed as described in Example 1, except that 104.2 mg (1.00 mmol) of styrene is used, and the reaction mixture is stirred at 150° C. for 8 hours. With 88.7% conversion of Cl-benzene, a 78% yield of Heck products (86.5% trans-stilbene, 0.3% cis-stilbene, 13.2% 1,1-diphenylethene) is obtained.

Example 6

A reaction is performed as described in Example 1, except that 102.8 mg (0.99 mmol) of styrene and 164.8 mg (1.46 mmol) of chlorobenzene are used, and the reaction mixture is stirred at 150° C. for 5.5 hours. With 94.6% conversion of Cl-benzene, an 82.1% yield of Heck products (86.7% trans-stilbene, 0.9% cis-stilbene, 12.4% 1,1-diphenylethene) is obtained.

Example 7

A reaction is performed as described in Example 1, except that 13.9 mg (0.02 mmol) of $(Ph_3P)_2PdCl_2$ and 29.9 mg (0.08 mmol) of $ph_4PCl$ in 1 ml of DMF is used as the catalyst. Stirring is performed at 150° C. for 5.5 hours. With 77.2% conversion of cl-benzene, a 69.6% yield of Heck products (84.7% trans-stilbene, 0.8% cis-stilbene, 14.5% 1,1-diphenylethene) is obtained.

Example 8

A reaction is performed as described in Example 1, except that 18.5 mg (0.02 mmol) of $(Ph_4P)_2PdCl_4$ (preparation as in Example A) to which 0.08 mmol of $Ph_4PCl$ has been added is used as the catalyst in 1 ml of DMF. Stirring is performed at 120° C. for 0.3 hours and at 150° C for 12 hours. With 80% conversion of Cl-benzene, an 85.1% yield of Heck products (86.1% trans-stilbene, 0.9% cis-stilbene, 13.0% 1,1-diphenylethene) is obtained.

Example 9

A reaction is performed as described in Example 1, except that 9.6 mg (0.02 mmol) of $[PPh_3PdPh(\mu\text{-Cl})]_2$ (preparation as in Example B) to which 44.98 mg (0.121 mmol) of $Ph_4PCl$ has been added is used as the catalyst in 1 ml of NMP. Stirring is performed at 150° C. for 12 hours. With 86.2% conversion of Cl-benzene, an 86.4% yield of Heck products (84.8% trans-stilbene, 0.9% cis-stilbene, 14.4% 1,1-diphenylethene) is obtained.

Example 10

A reaction is performed as described in Example 1, except that 5.6 mg (0.02 mmol) of Pd(tetramethylethylenediamine)$Me_2$ and 46.0 mg (0.12 mmol) of $Ph_4PCl$ to which 9.9 mg (0.1 mmol) of dimethylglycine has been added is used as the catalyst. Stirring is performed at 150° C. for 12 hours. With 84.9% conversion of Cl-benzene, an 81.5% yield of Heck products (96.8% trans-stilbene, 0.7% cis-stilbene, 2.5% 1,1-diphenylethene) is obtained.

Example 11

A reaction is performed as described in Example 1, except that 18.6 mg (0.02 mmol) of Pd(dibenzylideneacetone)$_2$ and 45.0 mg (0.12 mmol) of Ph$_4$PCl in 1 ml of DMF is used as the catalyst. Stirring is performed at 150° C. for 6 hours. With 26.5% conversion of Cl-benzene, a 34.2% yield of Heck products (84.3% trans-stilbene, 1.4% cis-stilbene, 14.4% 1,1-diphenylethene) is obtained.

Example 12

A reaction is performed as described in Example 1, except that 195.7 mg (2.04 mmol) of Na propionate in 1 ml of DMF is used as the base. Stirring is performed at 150° C. for 12 hours. With 73% conversion of Cl-benzene, a 55.1% yield of Heck products (84.0% trans-stilbene, 1.9% cis-stilbene, 14.9% 1,1-diphenylethene) is obtained.

Example 13

A reaction is performed as described in Example 12, except that 1 ml of NMP is used as the solvent. With 75% conversion of Cl-benzene, a 68.0% yield of Heck products (84.2% trans-stilbene, 1.9% cis-stilbene, 14.7% 1,1-diphenylethene) is obtained.

Example 14

A reaction is performed as described in Example 1, except that 144.3 mg (1.0 mmol) of Na benzoate in 1 ml of DMF is used as the base. Stirring is performed at 150° C. for 5.5 hours. With 52.4% conversion of Cl-benzene, a 55.5% yield of Heck products (84.4% trans-stilbene, 1.0% cis-stilbene, 14.7% 1,1-diphenylethene) is obtained.

Example 15

A reaction is performed as described in Example 14, except that 1 ml of NMP is used as the solvent. With 60% conversion of Cl-benzene, a 58.0% yield of Heck products (84.2% trans-stilbene, 1.9% cis-stilbene, 14.7% 1,1-diphenylethene) is obtained.

Example 16

A reaction is performed as described in Example 1, except that 311.6 mg (2.15 mmol) of Na picolate in 1 ml of DMF is used as the base. Stirring is performed at 150° C. for 12 hours. With 26.7% conversion of Cl-benzene, a 32.1% yield of Heck products (97–4% trans-stilbene, 1.1% cis-stilbene, 1.5% 1,1-diphenylethene) is obtained.

Example 17

A reaction is performed as described in Example 16, except that 1 ml of NMP is used as the solvent. With 31.59% conversion of Cl-benzene, a 34.0%- yield of Heck products (84.2% trans-stilbene, 1.9% cis-stilbene, 14.7% 1,1-diphenylethene) is obtained.

Example 18

A reaction is performed as described in Example 1, except that 12.5 mg (0.12 mmol) of dimethylglycine is added to the first two educts as an additive. Stirring is performed at 120° C. for 30 minutes and at 150° C. for 12 hours. With 95.6% conversion of Cl-benzene, a 100% yield of Heck products (96.4% trans-stilbene, 0.7% cis-stilbene, 2.9% 1,1-diphenylethene) is obtained.

Example 19

A reaction is performed as described in Example 18, except that 1 ml of DMF is used as the solvent. With 95.2% conversion of Cl-benzene, an 83.6% yield of Heck products (96.4% trans-stilbene, 0.7% cis-stilbene, 2.9% 1,1-diphenylethene) is obtained.

Example 20

A reaction is performed as described in Example 1, except that 13.9 mg (0.02 mmol) of (Ph$_3$P)$_2$PdCl$_2$ and 29.9 mg (0.08 mmol) of Ph$_4$PCl in 1 ml of NMP to which 9.9 mg (0.1 mmol) of dimethylglycine has been added is used as the catalyst. Stirring is performed at 150° C. for 12 hours. With 81.4% conversion of Cl-benzene, a 79.6% yield of Heck products (96.81% trans-stilbene, 0.71% cis-stilbene, 2.5% 1,1-diphenylethene) is obtained.

Example 21

A reaction is performed as described in Example 1, except that 9.6 mg (0.02 mmol) of [PPh$_3$PdPh($\mu$-Cl)]$_2$ to which 44.98 mg (0.12 mmol) of Ph$_4$PCl has been added is used as the catalyst in 1 ml of NMP to which 9.8 mg (0.1 mmol) of dimethylglycine is added. Stirring is performed at 150° C. for 12 hours. With 89.2% conversion of Cl-benzene, an 87.4% yield of Heck products (99.9% trans-stilbene, 0.9% cis-stilbene, 2.2% 1,1-diphenylethene) is obtained.

Example 22

A reaction is performed as described in Example 1, except that 0.02 mmol of the catalyst solution described in Example C to which 44.98 mg (0.12 mmol) of Ph$_4$PCl has been added is used as the catalyst in 1 ml of NMP. Stirring is performed at 150° C. for 12 hours. With 82.4% conversion of Cl-benzene, an 83.5% yield of Heck products (96.9% trans-stilbene, 0.9% cis-stilbene, 2.2% 1,1-diphenylethene) is obtained.

Example 23

A reaction is performed as described in Example 1, except that 6.7 mg (0.02 mmol) of the catalyst described in Example D to which 45 mg (0.12 mmol) of Ph$_4$PCl has been added is used as the catalyst in 1 ml of NMP. Stirring is performed at 150° C. for 12 hours. With 91.5% conversion of Cl-benzene, an 89.7% yield of Heck products (96.7% trans-stilbene, 0.9% cis-stilbene, 2.4% 1,1-diphenylethene) is obtained.

Example 24

A reaction is performed as described in Example 1, except that 64.1 mg (0.02 mmol) of the catalyst described in Example E is used in 1 ml of NMP. Stirring is performed at 150° C. for 12 hours. With 98.2% conversion of Cl-benzene, a 97.6% yield of Heck products (97.1% trans-stilbene, 0.9% cis-stilbene, 2.0% 1,1-diphenylethene) is obtained.

Example 25

A reaction is performed as described in Example 1, except that 18.5 mg (0.02 mmol) of (Ph$_4$P)$_2$PdCl$_4$ to which 30.0 mg (0.08 mmol) of Ph$_4$PCl has been added is used as the catalyst in 1 ml of DMF to which 9.6 mg (0.09 mmol) of dimethylglycinie is added. Stirring is performed at 120° C. for 0.3 hours and at 150° C. for 12 hours. With 98% conversion of Cl-benzene, a 97.4% yield of Heck products (96.1% trans-stilbene, 0.9% cis-stilbene, 3.0% 1,1-diphenylethene) is obtained.

Example 26

A reaction is performed as described in Example 1, except that 14.8 mg (0.12 mmol) of picolinic acid is used as the additive, and stirring is performed only at 150° C. for 12 hours. With 65.6% conversion of Cl-benzene, a 70.1% yield of Heck products (96.9% trans-stilbene, 0.9% cis-stilbene, 2.2% 1,1-diphenylethene) is obtained.

Example 27

A reaction is performed as described in Example 26, except that 1 ml of DMF is used as the solvent. With 89.0% conversion of Cl-benzene, an 81% yield of Heck products (96.9% trans-stilbene, 0.9% cis-stilbene, 2.2% 1,1-diphenylethene) is obtained.

Example 28

A reaction is performed as described in Example 1, except that 50.3 mg of $Ph_4PBr$ (0.12 mmol) is used instead of $Ph_4PCl$, and 1 ml of DMF is used as the solvent. With 74.8% conversion of Cl-benzene, a 77.3% yield of Heck products (85.9% trans-stilbene, 0.6% cis-stilbene, 13.5% 1,1-diphenylethene) is obtained.

Example 29

A reaction is performed as described in Example 1, except that 47.8 mg (0.12 mmol) of $Ph_4POAc$ is used as the phosphonium salt in 1 ml of DMF. Stirring is performed at 150° C. for 12 hours. With 73.5% conversion of Cl-benzene, a 71.9% yield of Heck products (85.7% trans-stilbene, 0.9t cis-stilbene, 13.4% 1,1-diphenylethene) is obtained.

Example 30

A reaction is performed as described in Example 1, except that 15.7 mg (0.12 mmol) of piperidine-2-carboxylic acid is used as the additive. With 84% conversion of Cl-benzene, an 87% yield of Heck products (96.2% trans-stilbene, 0.8% cis-stilbene, 2.97% 1,1-diphenylethene) is obtained.

Example 31

A reaction is performed as described in Example 1, except that 14.1 mg (0.12 mmol) of proline is used as the additive, and stirring is performed only at 150° C. for 12 hours. With 69.4% conversion of Cl-benzene, a 71.1% yield of Heck products (94.7% trans-stilbene, 0.1% cis-stilbene, 4.4% 1,1-diphenylethene) is obtained.

Example 32

A reaction is performed as described in Example 31, except that 1 ml of DMF is used as the solvent. With 89.6% conversion of Cl-benzene, an 82.6% yield of Heck products (92.3% trans-stilbene, 0.8% cis-stilbene, 6.8% 1,1-diphenylethene) is obtained.

Example 33

A reaction is performed as described in Example 1, except that 3.8 mg (0.015 mmol) of $(CH_3CN)_2PdCl_2$ and 34.0 mg (0.09 mmol) of $Ph_4PCl$ as the catalyst and 147.1 mg (1.86 mmol) of pyridine as the additive are reacted. Stirring is performed at 150° C. for 20 hours. With 86.4% conversion of Cl-benzene, a 67.9% yield of Heck products (91.69 trans-stilbene, o.6% cis-stilbene, 7.8% 1,1-diphenylethene) is obtained.

Example 34

To a reaction vessel standing on a scale which is sealed with a septum cap, 5.3 mg (0.02 mmol) of $(CH_3CN)_2PdCl_2$, 45 mg (0.12 mmol) of $Ph_4PCl$ and 12.4 mg (0.12 mmol) of dimethylglycine are added, followed by two cycles of evacuation and flushing with argon. Under argon, 657.7 mg (8 mmol) of anhydrous sodium acetate and 1 ml of NMP are added. 452 mg (4.01 mmol) of Cl-benzene and 636 mg (6.11 mmol) of styrene is mixed with 1 ml of NMP and added dropwise in 6 portions within 6 hours, the first portion being added at room temperature and the others at 140° C. Stirring is performed at 140° C. for a total of 24 h. According to the processing described in Example 1 using 10 ml of diethyl ether, a 64.2% yield of Heck products (97.4% trans-stilbene, 0.6% cis-stilbene, and 2.0%- 1,1-diphenylethene) is obtained with 76.6% conversion of Cl-benzene.

Example 35

A reaction is performed as described in Example 1, except that 3.9 mg (0.015 mmol) of $(CH_3CN)_2PdCl_2$, 34.9 mg (0.09 mmol) of $Ph_4PCl$, 520.9 mg (6.35 mmol) of anhydrous sodium acetate, 499.6 mg (3.118 mmol) of Br-benzene and 489.3 mg (4.7 mmol) of styrene are reacted in 1.5 ml of DMF. Stirring is performed at 130° C. for 5 hours. According to the processing described in Example 1, a 74.8% yield of Heck products (85.0% trans-stilbene, 0.5% cis-stilbene, and 14.5% 1,1-diphenylethene) is obtained with 74.6% conversion of Br-benzene.

Example 36

A reaction is performed as described in Example 1, except that 503.5 mg (3.2 mmol) of p-nitrochlorobenzene and 493.9 mg (4.74 mmol) of styrene are reacted in 1.5 ml of DMF. As the catalyst, 3.9 mg (0.015 mmol) of $(CH_3CN)_2PdCl_2$ and 34.9 mg (0.093 mmol) of $Ph_4PCl$ is used. Stirring is performed at 135° C. for 12 hours. According to the processing described in Example 1, a 15.9% yield of Heck products is obtained with 68.5% conversion of p-nitrochlorobenzene.

Example 37

A reaction is performed as described in Example 1, except that 124.7 mg (0.99 mmol) of p-chlorotoluene and 113.7 mg (1.09 mmol) of styrene are reacted in 1 ml of DMP. As the catalyst, 10.4 mg (0.04 mmol) of $(CH_3CN)_2PdCl_2$ and 89.6 mg (0.24 mmol) of $Ph_4PCl$ is used. Stirring is performed at 150° C. for 4.3 hours. According to the processing described in Example 1, a 22.9% yield of Heck products is obtained with 70.7% conversion of p-chlorotoluene.

Example 38

A reaction is performed as described in Example 1, except that 160.1 mg (1.036 mmol) of p-chloroacetophenone and 125.8 mg (1.21 mmol) of styrene are reacted in 1 ml of NMP. As the catalyst, 5.1 mg (0.02 mmol) of $(CH_3CN)_2PdCl_2$ and 44.8 mg (0.12 mmol) of $Ph_4PCl$ is used. Stirring is performed at 120° C. for 0.5 hours and at 150° C. for 12 hours. According to the processing described in Example 1, a 48.2% yield of Heck products is obtained with 74.6% conversion of p-chloroacetophenone.

Example 39

A reaction is performed as described in Example 1, except that 3.9 mg (0.015 mmol) of $(CH_2CN)_2PdCl_2$, 34.9 mg (0.09 mmol) of $Ph_4PCl$, 496.0 mg (6.05 mmol) of anhydrous sodium acetate, 638.74 mg (3.07 mmol) of 3-bromoquinoline and 427.0 mg (4.1 mmol) of styrene are reacted in 1.5 ml of DMF. Stirring is performed at 130° C. for 5 hours. According to the processing described in Example 1, a 72.5% yield of Heck products (85.1% trans-stilbene, 0.8% cis-stilbene, and 14.1% 1,1-diphenylethene) is obtained with 78.5% conversion of 3-bromoquinoline.

Examples with Acrylates and Br- or Cl-aromatics

Example 40

To a reaction vessel standing on a scale, 5.1 mg (0.02 mmol) of $(CH_2CN)_2PdCl_2$ and 45 mg (0.12 mmol) of $Ph_4PCl$ are added, followed by two cycles of evacuation and flushing with argon. Under argon, 147.7 mg (1.8 mmol) of anhydrous sodium acetate, 110.4 mg (0.98 mmol) of chlorobenzene and 184.2 mg (1.0 mmol) of ethylhexyl acrylate are added. After the addition of 1 ml of NMP, the vessel is sealed, and the mixture is stirred first at 120° C. for 60 minutes and then at 150° C. for 20 hours.

After the reaction, the GC standards n-decane and n-hexadecane are added, and 3 ml of diethyl ether is added to the mixture. After filtering off the solids, the filtrate is examined by gas chromatography: With 31.6% conversion of Cl-benzene, a 34.6% yield of Heck product is obtained.

Example 41

A reaction is performed as described in Example 40, except that 5.0 mg (0.019 mmol) of $(CH_3CN)_2PdCl_2$, 45 mg (0.12 mmol) of $Ph_4PCl$, 177.2 mg (2.16 mmol) of sodium acetate, 116.4 mg (1.03 mmol) of chlorobenzene, 152.9 mg (1.193 mmol) of butyl acrylate and 1 ml of DMF are used. Stirring is performed at 160° C. for 5.5 hours. With 29.5% conversion of Cl-benzene, a 14.8% yield of Heck product is obtained.

Example 42

A reaction is performed as described in Example 40, except that 5.3 mg (0.02 mmol) of $(CH_3CN)_2PdCl_2$, 45.2 mg (0.12 mmol) of $Ph_4PCl$, 185.4 mg (2.26 mmol) of sodium acetate, 120.3 mg (1.07 mmol) of chlorobenzene, 189.4 mg (1.48 mmol) of tert-butyl acrylate and 1 ml of NMP are used. Stirring is performed at 120° C. for 1 hour and at 150° C. for 20 hours. With 28.7% conversion of Cl-benzene, a 27.5% yield of Heck product is obtained.

Example 43

A reaction is performed as described in Example 40, except that 5.1 mg (0.02 mmol) of $(CH_3CN)_2PdCl_2$, 45 mg (0.12 mmol) of $Ph_4PCl$, 228 mg (2.8 mmol) of sodium acetate, 120.0 mg (1.07 mmol) of chlorobenzene, 337.8 mg (1.70 mmol) of ethylhexyl methacrylate and 1 ml of DMF are used. With 93% conversion of Cl-benzene, an about 40% yield of Heck product is obtained.

Example 44

A reaction is performed as described in Example 40, except that 1.3 mg (0.005 mmol) of $(CH_3CN)_2PdCl_2$, 11.9 mg (0.032 mmol) of $Ph_4PCl$, 1.676 g (20.43 mmol) of sodium acetate, 1.54 g (9.81 mmol) of Br-benzene, 1.86 g (14.48 mmol) of butyl acrylate and 5 ml of DMF are used. For the processing, 10 ml of diethyl ether is used. With 100% conversion of Br-benzene, a 92.3% yield of Heck product is obtained.

Example 45

A reaction is performed as described in Example 40, except that 5.4 mg (0.02 mmol) of $(CH_3CN)_2PdCl_2$, 45 mg (0.12 mmol) of $Ph_4PCl$, 175 mg (2.13 mmol) of sodium acetate, 196.9 mg (1.05 mmol) of p-Br-anisole, 328.9 mg (1.79 mmol) of ethylhexyl acrylate and 1 ml of NMP are used. With 100% conversion of p-Br-anisole, a 90% yield of Heck product is obtained.

Examples with Cyclofrexene and Haloaromatics

Example 46

A reaction is performed as described in Example 1, except that 162.6 mg (1.04 mmol) of bromobenzene and 121.9 mg (1.48 mmol) of cyclohexene are reacted with the same catalyst in 1 ml of NMP to which 14.1 mg (0.14 mmol) of dimethylglycine is added as the additive. Stirring is performed at 140° C. for 8 hours. With 38.5% conversion of bromobenzene, a 30.9% yield of Heck products (double bond isomer ratio of 48.4:51.6) is obtained.

Example 47

A reaction is performed as described in Example 1, except that 115.9 mg (1.03 mmol) of chlorobenzene and 120.0 mg (1.4 mmol) of cyclohexene are reacted with the same catalyst in 1 ml of NMP to which 13.0 mg (0.13 mmol) of dimethylglycine is added. Stirring is performed at 150° C. for 12 hours. With 22.3% conversion of chlorobenzene, a 17.7% yield of Heck products (double bond isomer ratio of 28.4:71.6) is obtained.

Example 48

A reaction is performed as described in Example 1, except that 212.1 mg (1.07 mmol) of bromoacetophenone and 122.7 mg (1.49 mmol) of cyclohexene are reacted with the same catalyst in 1 ml of NMP to which 14.7 mg (0.14 mmol) of dimethylglycine is added. Stirring is performed at 140° C. for 8 hours. With about 10% conversion of bromoacetophenone, a 10.3% yield of Heck products (double bond isomer ratio of 43.7:56.3) is obtained.

Example with Ethylene and Haloaromatics

Example 49

11.85 g (50 mmol) of 2-bromo-6-methoxynaphthalene is dissolved in 50 ml of DMP and transferred to a 100 ml stainless steel autoclave equipped with a magnetic stirrer together with 8.2 g (100 mmol) of NaOAc, 260 mg (1 mmol) of $(CH_3CN)_2PdCl_2$ and 225.1 mg (6 mmol) of $Ph_4PCl$. Stirring is performed for 14 hours under an ethylene pressure of 20 bar. Yield of 2-vinyl-6-methoxynaphthalene: 78%.

What is claimed is:

1. A process for the preparation of an olefin-substituted aromatic or heteroaromatic of formula III

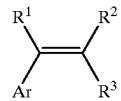

III wherein Ar represents a substituted or unsubstituted aryl or heteroaryl group, and $R^1$, $R^2$ and $R^3$ independently represent hydrogen, alkyl-$(C_1$–$C_8)$, phenyl, 1- or 2-naphthyl, vinyl, O-alkyl-$(C_1$–$C_8)$, O-phenyl, CN, $CO_2H$, $CO_2$-alkyl-$(C_1$–$C_8)$, $CO_2$-phenyl, $CONH_2$, CONH-alkyl-$(C_1$–$C_5)$, CON(alkyl)$_2$-$(C_1$–$C_5)$, fluoro, chloro, PO(phenyl)$_2$, PO(alkyl)$_2$-(C$_1$–C$_5$), CO-phenyl, CO-alkyl-(C$_1$–C$_5$), NH-alkyl-(C$_1$–C$_4$), SO$_3$H, PO$_3$H, SO$_3$-alkyl-(C$_1$–C$_4$) or SO$_2$-alkyl-(C$_1$–C$_4$), or R$^1$+R$^2$=(CH$_2$), or R$^2$+R$^3$=(CH$_2$)$_n$ wherein n=2–16, comprising reacting an aromatic or heteroaromatic of formula I ArX      I wherein Ar has the same meaning as in formula III and X represents chloro, bromo, OSO$_2$CH$_3$, OSO$_2$-tolyl, OSO$_2$CF$_3$ or OSO$_2$C$_4$F$_9$, with an olefin of formula II

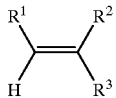

II wherein R$^1$, R$^2$ and R$^3$ have the same meanings as in formula III, in the presence of a palladium catalyst, wherein said palladium catalyst comprises a palladium (II) compound of the formula PdXY or a CH$_3$CN, C$_6$H$_5$CN or P(C$_6$H$_5$)$_3$ complex therewith, wherein X=Y =Cl, Br, I, RCO$_2$ (R=C$_1$–C$_{22}$, CF$_3$, CCl$_3$, CH$_2$OCH$_3$, C$_6$H$_5$) or RSO$_3$ (R=C$_1$–C$_{22}$, CF$_3$, C$_4$F$_9$, CCl$_3$, C$_6$H$_5$, p—CH$_3$C$_6$H$_4$), in the presence of a tetraarylphosphonium salt Ar$^1$Ar$^2$Ar$^3$Ar$^4$P$^+$Z$^-$, wherein Ar$^1$, Ar$^2$, Ar$^3$ and Ar$^4$ represent identical or different aryl groups, and Z=Cl, Br, RCO$_2$ (R=C$_1$–C$_{22}$, CF$_3$, CCl$_3$, C$_6$H$_5$) or RSO$_3$ (R=C$_1$–C$_{22}$, CF$_3$, C$_4$F$_9$, C$_6$H$_5$, p—CH$_3$C$_6$H$_4$), and said reacting is performed in the presence of a dipolar aprotic solvent and a base, in the presence or absence of an additive selected from the group consisting of nitrogen-containing carboxylic acids and aromatic nitrogen-containing heterocycles, at a temperature of from 60° C. to 180° C.

2. The process according to claim 1, wherein said palladium catalyst comprises a palladium(II) compound of formula PdXY or a CH$_3$CN, C$_6$H$_5$CN or P(C$_6$H$_5$)$_3$ complex therewith in monomeric or oligomeric form, wherein X=Cl, Br, I, RCO$_2$ [R=C$_1$–C$_{22}$, CF$_3$, CCl$_3$, CH$_2$N(CH$_3$)$_2$, C$_6$H$_5$] or RSO$_3$ (R=C$_1$–C$_{22}$, CF$_3$, C$_4$F$_9$, CCl$_3$, C$_6$H$_5$, p—CH$_3$C$_6$H$_4$), and Y=C$_6$H$_5$, o-, m-, p—CH$_3$C$_6$H$_4$, o-, m-, p—Cl—C$_6$H$_4$, o-, m-, p—CHOC$_6$H4, o-, m-, p—CN—C$_6$H$_4$, o-, m-, p—NO$_2$—C$_6$H$_4$, o-, m-, p—PhCO—C$_6$H$_4$, o-, m-, p—F—C$_6$H$_4$, 1-C$_{10}$H$_7$ or 2-C$_{10}$H$_7$, in the presence of a tetraarylphosphonium salt Ar$^1$Ar$^2$Ar$^3$Ar$^4$P$^+$Z$^-$, wherein Ar$^1$, Ar$^2$, Ar$^3$ and Ar$^4$ represent identical or different aryl groups, and Z=Cl, Br, RCO$_2$ (R=C$_1$–C$_{22}$, CF$_3$, CCl$_3$, C$_6$H$_5$) or RSO$_3$ (R=C$_1$–C$_{22}$, CF$_3$, C$_4$F$_9$, C$_6$H$_5$, p—CH$_3$C$_6$H$_4$), and said reacting is performed in the presence of a dipolar aprotic solvent and a base, in the presence or absence of an additive selected from the group consisting of nitrogen-containing carboxylic acids and aromatic nitrogen-containing heterocycles, at a temperature of from 60° C. to 180° C.

3. The process according to claim 1, wherein the ratio of PdX$_2$ or PdXY to the phosphonium salt Ar$^1$Ar$^2$Ar$^3$Ar$^4$P$^+$Z$^-$ is from 1:1 to 1:10.

4. The process according to claim 1, wherein the dipolar aprotic solvent is dimethylsulfoxide, dimethylformamide, dimethylacetamide, 1,3-dimethyl-3,4,5,6-tetrahydro-2(1H)-pyrimidone or N-methylpyrrolidone.

5. The process of claim 1, wherein the base is an amine, an alkali or alkaline earth metal salt of a carboxylic acid or an alkali or alkaline earth metal carbonate or bicarbonate.

6. The process according to claim 1, wherein said reacting is performed in a temperature range of from 60 to 180° C.

7. The process according to claim 1, wherein said reacting is performed in the presence of a selectivity-enhancing nitrogen-containing additive.

8. The process according to claim 7, wherein said additive is a nitrogen-containing carboxylic acid or its alkali or alkaline earth salt.

9. The process according to claim 7, wherein said additive is a nitrogen-containing heterocycle.

10. The process according to claim 8, wherein said additive is N,N-dimethylglycine.

11. The process according to claim 7, wherein said additive is pyridine.

12. The process according to claim 1, wherein said base is also a selectivity-enhancing nitrogen-containing additive selected from the group consisting of nitrogen-containing carboxylic acids and aromatic nitrogen-containing heterocycles.

13. The process according to claim 7, wherein the ratio of PdX$_2$ or PdXY to the additive is from 1:1 to 1:100.

14. The process according to claim 1, wherein in the tetraarylphosphonium salt Ar$^1$Ar$^2$Ar$^3$Ar$^4$ P$^+$Z$^-$, one or more of Ar$^1$, Ar$^2$, Ar$^3$ and Ar$^4$ represents C$_6$H$_5$, o-, m-, p—CH$_3$—C$_6$H$_4$, o-, m-, p—Cl—C$_6$H$_4$ or 1- or 2-C$_{10}$H$_7$.

15. The process according to claim 2, wherein the tetraarylphosphonium salt Ar$^1$Ar$^2$Ar$^3$Ar$^4$ P$^+$Z$^-$, one or more of Ar$^1$, Ar$^2$, Ar$^3$ and Ar$^4$ represents C$_6$H$_5$, o-, m-, p—CH$_3$—C$_6$H$_4$, o-, m-, p—Cl—C$_6$H$_4$ or 1- or 2-C$_{10}$—H$_7$.

* * * * *